US006310273B1

(12) United States Patent
Gilchrist et al.

(10) Patent No.: US 6,310,273 B1
(45) Date of Patent: Oct. 30, 2001

(54) INHIBITING APOPTOSIS IN PLANTS USING A BACULOVIRUS P35 PROTEASE INHIBITOR GENE

(75) Inventors: David G. Gilchrist, Winters; James E. Lincoln, Woodland; Craig Richael, Roseville, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/370,976

(22) Filed: Aug. 10, 1999

Related U.S. Application Data

(63) Continuation-in-part of application No. 09/132,290, filed on Aug. 11, 1998, now abandoned.

(51) Int. Cl.[7] .......................... C12N 15/82; C12N 15/90; C12N 5/04; A01H 5/00

(52) U.S. Cl. ......................... 800/279; 435/69.1; 435/468; 800/288; 800/301; 800/306; 800/317; 800/320

(58) Field of Search .................................. 435/69.1, 468, 435/410, 419; 800/278, 279, 288, 295, 298, 301, 306, 313, 317, 320

(56) References Cited

U.S. PATENT DOCUMENTS

| | | | |
|---|---|---|---|
| 5,798,442 | 8/1998 | Gallant et al. ....................... | 530/330 |
| 5,834,228 | 11/1998 | Becker et al. ......................... | 435/23 |

OTHER PUBLICATIONS

Birnbaum, M.J. et al., "An Apoptosis–Inhibiting Gene from a Nuclear Polyhedrosis Virus Encoding a Polypeptide with Cys/His Sequence Motifs," *J. Virology*, 68:2521–2528 (1994).

Bump, N.J. et al., "Inhibition of ICE Family Proteases by Baculovirus Antiapoptotic Protein p35" *Science*, 269:1885–1888 (1995).

Clem, R.J. et al., "Prevention of Apoptosis by a Baculovirus Gene During Infection of Insect Cells" *Science* 254:1388–1390 (1991).

Dinigan, D.D. et al., "Suppression of the TMV–mediated hypersensitive response by the baculovirus p35 inhibitor of apoptosis protein," *American Society for Virology*, 16th Annual Mtg., Montana State University, Bozeman, Montana, Abstract W11–9, Jul. 19–23 (1997).

Kamita, S.G. et al., "Identification and Characterization of the p35 Gene of *Bombyx mori* Nuclear Polyhedrosis Virus That Prevents Virus–Induced Apoptosis," *J. Virology*, 67:455–463 (1993).

Wang, H. et al., "Apoptosis: A Functional Paradigm for Programmed Plant Cell Death Induced by a Host–Selective Phytotoxin and Invoked during Development," The Plant Cell, 8:375–391 (1996).

Ding, X. et al., "Insect resistance of transgenic tobacco expressing an insect chitinase gene," *Transgenic Research*, 7:77–84 (1998).

Adang, M.J. et al., "The reconstruction and expression of a *Bacillus thuringiensis* cryIIIA gene in protoplasts and potato plants," *Plant Molecular Biology*, 21:1131–1145 (1993).

Mittler, R. et al., "Pathogen–induced Programmed Cell Death in Plants, a Possible Defense Mechanism," *Developmental Genetics*, 21:279–289 (1997).

D'Silva, I. et al., "Activation of Cysteline Proteases in Cowpea Plants during the Hypersensitive Response—A Form of Programmed Cell Death," *Experimental Cell Research*, 245:389–399 (1998).

Spinedi, A. et al., "Ceramide–Induced Apoptosis Is Mediated by Caspase Activation Independently from Retinoblastoma Protein Post–Translational Modification," *Biochemical and Biophysical Research Communications*, 243:852–857 (1998).

Hawkins, C.J. et al., "Inhibition of interleukin 1β–converting enzyme–mediated apoptosis of mammalian cells by baculovirus 1AP," *Proc. Natl. Acad. Sci. USA*, 93:13786–13790 (1996).

Miura, M. et al., "Tumor necrosis factor–induced apoptosis is mediated by a CrmA–sensitive cell death pathway," *Proc. Natl. Acad. Sci. USA*, 92:8318–8322 (1995).

Seshagiri, S. et al., "Baculovirus inhibitors of apoptosis (IAPs) block activiation of Sf–caspase–1" *Proc. Natl. Acad. Sci. USA*, 94:13606–13611 (1997).

Heath, M.C., "Apoptosis, Programmed Cell Death and the Hypersensitive Response," *Eur. J. Plant Pathol*, 104(2):117–124 (Mar. 1998).

Pozo, et al., "Caspases and Programmed Cell Death in the Hypersensitive Response of Plants to Pathogens," *Curr. Biol. 28*, 8(20):1129–1132 (Sep. 1998).

*Primary Examiner*—Amy J. Nelson
*Assistant Examiner*—Ashwin D. Mehta
(74) *Attorney, Agent, or Firm*—Townsend and Townsend and Crew LLP

(57) ABSTRACT

This invention relates to methods of inhibiting apopotosis in plants in plants using a baculovirus p35 protease inhibitor gene. This method can impart improved pathogen resistance to pathogens that exploit apoptosis as a part of the infection process.

8 Claims, 2 Drawing Sheets

SEQUENCE LISTING

<160> NUMBER OF SEQ ID NOS: 5

<210> SEQ ID NO 1
<211> LENGTH: 900
<212> TYPE: DNA
<213> ORGANISM: Autographa californica nucleopolyhedrovirus
<220> FEATURE:
<221> NAME/KEY: CDS
<222> LOCATION: (1)..(900)
<223> OTHER INFORMATION: cysteine dependent aspartate cleaving protease
      (caspase) inhibitor p35 of AcNPV

<400> SEQUENCE: 1

```
atg tgt gta att ttt ccg gta gaa atc gac gtg tcc cag acg att att      48
Met Cys Val Ile Phe Pro Val Glu Ile Asp Val Ser Gln Thr Ile Ile
 1               5                  10                  15 cga gat tgt cag gtg gac aaa caa acc aga gag ttg gtg tac att aac      96
Arg Asp Cys Gln Val Asp Lys Gln Thr Arg Glu Leu Val Tyr Ile Asn
            20                  25                  30 aag att atg aac acg caa ttg aca aaa ccc gtt ctc atg atg ttt aac     144
Lys Ile Met Asn Thr Gln Leu Thr Lys Pro Val Leu Met Met Phe Asn
        35                  40                  45 att tcg ggt cct ata cga agc gtt acg cgc aag aac aac aat ttg cgc     192
Ile Ser Gly Pro Ile Arg Ser Val Thr Arg Lys Asn Asn Asn Leu Arg
    50                  55                  60 gac aga ata aaa tca aaa gtc gat gaa caa ttt gat caa cta gaa cgc     240
Asp Arg Ile Lys Ser Lys Val Asp Glu Gln Phe Asp Gln Leu Glu Arg
65                  70                  75                  80 gat tac agc gat caa atg gat gga ttc cac gat agc atc aag tat ttt     288
Asp Tyr Ser Asp Gln Met Asp Gly Phe His Asp Ser Ile Lys Tyr Phe
                85                  90                  95 aaa gat gaa cac tat tcg gta agt tgc caa aat ggc agc gtg ttg aaa     336
Lys Asp Glu His Tyr Ser Val Ser Cys Gln Asn Gly Ser Val Leu Lys
```

-continued

```
          100                 105                 110
agc aag ttt gct aaa att tta aag agt cat gat tat acc gat aaa aag      384
Ser Lys Phe Ala Lys Ile Leu Lys Ser His Asp Tyr Thr Asp Lys Lys
        115                 120                 125 tct att gaa gct tac gag aaa tac tgt ttg ccc aaa ttg gtc gac gaa      432
Ser Ile Glu Ala Tyr Glu Lys Tyr Cys Leu Pro Lys Leu Val Asp Glu
    130                 135                 140 cgc aac gac tac tac gtg gcg gta tgc gtg ttg aag ccg gga ttt gag      480
Arg Asn Asp Tyr Tyr Val Ala Val Cys Val Leu Lys Pro Gly Phe Glu
145                 150                 155                 160 aac ggc agc aac caa gtg cta tct ttc gag tac aac ccg att ggt aac      528
Asn Gly Ser Asn Gln Val Leu Ser Phe Glu Tyr Asn Pro Ile Gly Asn
                165                 170                 175 aaa gtt att gtg ccg ttt gct cac gaa att aac gac acg gga ctt tac      576
Lys Val Ile Val Pro Phe Ala His Glu Ile Asn Asp Thr Gly Leu Tyr
            180                 185                 190 gag tac gac gtc gta gct tac gtg gac agt gtg cag ttt gat ggc gaa      624
Glu Tyr Asp Val Val Ala Tyr Val Asp Ser Val Gln Phe Asp Gly Glu
        195                 200                 205 caa ttt gaa gag ttt gtg cag agt tta ata ttg ccg tcg tcg ttc aaa      672
Gln Phe Glu Glu Phe Val Gln Ser Leu Ile Leu Pro Ser Ser Phe Lys
    210                 215                 220 aat tcg gaa aag gtt tta tat tac aac gaa gcg tcg aaa aac aaa agc      720
Asn Ser Glu Lys Val Leu Tyr Tyr Asn Glu Ala Ser Lys Asn Lys Ser
225                 230                 235                 240 atg atc tac aag gct tta gag ttt act aca gaa tcg agc tgg ggc aaa      768
Met Ile Tyr Lys Ala Leu Glu Phe Thr Thr Glu Ser Ser Trp Gly Lys
                245                 250                 255 tcc gaa aag tat aat tgg aaa att ttt tgt aac ggt ttt att tat gat      816
Ser Glu Lys Tyr Asn Trp Lys Ile Phe Cys Asn Gly Phe Ile Tyr Asp
            260                 265                 270 aaa aaa tca aaa gtg ttg tat gtt aaa ttg cac aat gta act agt gca      864
Lys Lys Ser Lys Val Leu Tyr Val Lys Leu His Asn Val Thr Ser Ala
        275                 280                 285 ctc aac aaa aat gta ata tta aac aca att aaa taa                      900
Leu Asn Lys Asn Val Ile Leu Asn Thr Ile Lys
    290                 295                 300

<210> SEQ ID NO 2
<211> LENGTH: 299
<212> TYPE: PRT
<213> ORGANISM: Autographa californica nucleopolyhedrovirus

<400> SEQUENCE: 2

Met Cys Val Ile Phe Pro Val Glu Ile Asp Val Ser Gln Thr Ile Ile
1               5                   10                  15

Arg Asp Cys Gln Val Asp Lys Gln Thr Arg Glu Leu Val Tyr Ile Asn
            20                  25                  30

Lys Ile Met Asn Thr Gln Leu Thr Lys Pro Val Leu Met Met Phe Asn
        35                  40                  45

Ile Ser Gly Pro Ile Arg Ser Val Thr Arg Lys Asn Asn Asn Leu Arg
    50                  55                  60

Asp Arg Ile Lys Ser Lys Val Asp Glu Gln Phe Asp Gln Leu Glu Arg
65                  70                  75                  80

Asp Tyr Ser Asp Gln Met Asp Gly Phe His Asp Ser Ile Lys Tyr Phe
                85                  90                  95

Lys Asp Glu His Tyr Ser Val Ser Cys Gln Asn Gly Ser Val Leu Lys
            100                 105                 110
```

```
Ser Lys Phe Ala Lys Ile Leu Lys Ser His Asp Tyr Thr Asp Lys Lys
        115                 120                 125

Ser Ile Glu Ala Tyr Glu Lys Tyr Cys Leu Pro Lys Leu Val Asp Glu
        130                 135                 140

Arg Asn Asp Tyr Tyr Val Ala Val Cys Val Leu Lys Pro Gly Phe Glu
145                 150                 155                 160

Asn Gly Ser Asn Gln Val Leu Ser Phe Glu Tyr Asn Pro Ile Gly Asn
                165                 170                 175

Lys Val Ile Val Pro Phe Ala His Glu Ile Asn Asp Thr Gly Leu Tyr
                180                 185                 190

Glu Tyr Asp Val Val Ala Tyr Val Asp Ser Val Gln Phe Asp Gly Glu
        195                 200                 205

Gln Phe Glu Glu Phe Val Gln Ser Leu Ile Leu Pro Ser Ser Phe Lys
        210                 215                 220

Asn Ser Glu Lys Val Leu Tyr Tyr Asn Glu Ala Ser Lys Asn Lys Ser
225                 230                 235                 240

Met Ile Tyr Lys Ala Leu Glu Phe Thr Thr Glu Ser Ser Trp Gly Lys
                245                 250                 255

Ser Glu Lys Tyr Asn Trp Lys Ile Phe Cys Asn Gly Phe Ile Tyr Asp
                260                 265                 270

Lys Lys Ser Lys Val Leu Tyr Val Lys Leu His Asn Val Thr Ser Ala
        275                 280                 285

Leu Asn Lys Asn Val Ile Leu Asn Thr Ile Lys
        290                 295

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:PCR
      primer for p35 from AcNPV

<400> SEQUENCE: 3
ggcaataaat tttaacattt atttaattgt g                              31

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:PCR
      primer for p35 from AcNPV

<400> SEQUENCE: 4
tgtgtaattt ttccggtaga aatcgac                                   27

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:cysteine
      dependent aspartate cleaving protease (caspase)
      family active site pentapeptide motif
<221> NAME/KEY: MOD_RES
<222> LOCATION: (4)
<223> OTHER INFORMATION: Xaa = Arg, Gln or Gly
```

```
<400> SEQUENCE: 5

Gln Ala Cys Xaa Gly
  1               5
```

INHIBITING APOPTOSIS IN PLANTS USING A BACULOVIRUS P35 PROTEASE INHIBITOR GENE

CROSS-REFERENCE TO RELATED APPLICATIONS

This application is a continuation-in-part and claims priority to U.S. patent application Ser. No. 09/132,290, filed Aug. 11, 1998 now abandoned, the specification of which is incorporated herein by reference.

STATEMENT AS TO RIGHTS TO INVENTIONS MADE UNDER FEDERALLY SPONSORED RESEARCH AND DEVELOPMENT

This invention was made with Government support under National Science Foundation Cooperative Agreement BIR-8920216. The Government has certain rights in this invention.

BACKGROUND OF THE INVENTION

FIELD OF THE INVENTION

This invention relates to methods of inhibiting apopotosis in plants using a caspase inhibitor. This method can impart improve pathogen resistance to pathogens that exploit apoptosis as a part of the infection process.

SUMMARY OF THE INVENTION

Figure 1A:
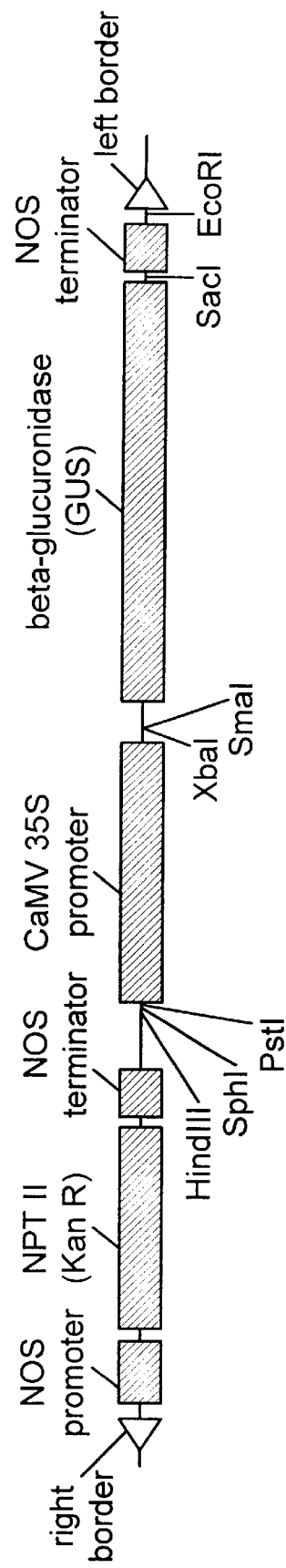
FIG. 1(a) is a map of the pBI121 which is a shuttle vector. (b) is a map of pPRM.-35K-ORF from which p35 was obtained. This plasmid was described by P. D. Friesen in *J. Virol.* 68:3467–3477 (1994).

This invention provides for a novel method of inhibiting apoptosis in a plant said method comprising the administration of a caspase inhibitor to the plant in an amount sufficient to inhibit apoptosis with the proviso that the caspase inhibitor is not Baculovirus p35 protease inhibitor. In one embodiment, the inhibitor is an amino blocked peptide with a reduced carboxy end. Examples of peptide inhibitors include Ac-DEVD-CHO, Ac-YVAD-CHO, Ac-DMQD-CHO and Ac-DQMD-CHO. Plants in which this invention has application include members of the family of *graminaceae, solanaceae, rosaceae, compositeae, leguminaceae, brassicaceae,* and *cucurbitaceae.*

The invention is applicable to fruit trees or vines. The inhibitors can be exogenously applied or supplied to a plant by genetic transformation. When exogenously applied the administration can be via foliar spraying.

The invention further provides for a composition suitable for horticultural application which comprises a caspase inhibitor and a surfactant where the inhibitor is present in an amount sufficient to inhibit apoptosis in a plant. The surfactant can be a detergent. The composition can be combined with other additives used in horticulture. The invention further provides for apparatus or systems including a spraying device and the inhibitor formulated to be sprayed upon a plant. The inhibitors can be peptides as described above.

This invention further provides for a method of increasing non-viral plant disease resistance in a plant said method comprising the expressing of a p35 protease inhibitor of baculovirus in the plant in an amount sufficient to increase non-viral plant disease resistance in the plant. Tobacco plants may be optionally excluded. The p35 or other peptides may be operably linked to an inducible plant promoter. The inhibitor gene is preferably expressed from a stably incorporated gene encoding p35 protease inhibitor wherein the gene has codons selected to be those preferably used by the host plant. The pathogens include both bacteria and fungi.

This invention further provides for a plant having increased plant disease resistance against non-viral pathogens wherein the increased plant disease resistance is due to the stable expression of a caspase protease inhibitor including the p35 protease inhibitor of baculovirus in the plant in an amount sufficient to increase non-viral plant disease resistance in the plant. Preferred plants are those described above.

Finally, this invention provides for a method for increasing the transformation rate of a plant cell with a heterologous gene by transfecting the cell with a gene encoding a caspase inhibitor such as p35 prior to transformation with the heterologous gene and transfecting the cell with the heterologous gene.

DETAILED DESCRIPTION

A. Introduction

This invention provides for method of inhibiting apoptosis in plants. Inhibiting apoptosis has importance from a practical and from a research perspective. Thinning of fruit, weed control and disease resistance in plant host interactions are practical uses. Research uses involve the controlled studies of apoptosis to define its role in germination, growth, development, flowering, seed production and infection by pathogens. Among the discoveries herein are the fact that caspase inhibitors are useful for preventing apoptosis, especially apoptosis induced by pathogens. It has been surprisingly discovered that caspase inhibitors and p35 protease inhibitors from baculoviruses will delay or suppress or inhibit an apoptosis response in plants to a number of stimuli. The suppressive effect on cell death extends to a wide range of fungal and bacterial pathogens. This research has identified a major paradigm shift in terms of the critical importance of apoptosis (induction of programmed cell death) in the infection process by most, if not all, pathogens that have traditionally been classified as necrotrophs. Conversely, the research leading to this discovery indicates that any method that blocks the ability of potential pathogens to trigger the induction of apoptosis has potential for disease control. This discovery has particular relevance in circumstances where non-viral plant pathogens induce and exploit apoptosis in plants as a part of the infection process. When a plant is transformed with caspase inhibitors, the plant will not be as susceptible to pathogen induced apoptosis and a resistance phenotype is generated.

This discovery has general application across the plant kingdom. It has been demonstrated by recombinant genetics and by exogenous application of the inhibitors. The use of caspase inhibitors to generate disease resistance is particularly useful for disease in which the plant has no known resistance gene.

In particular the examples provide specific plant/bacterial combinations and plant/fungal combinations where the invention is applicable. It is a diverse grouping of plants and pathogens. Bacterial pathogens include Psuedomonas and Xanthomonas. Fungal pathogens include *Sclerotinia sclerotiorum,* Alterneria species such as stem canker disease of tomato, and Fusarium sps.

B. Definitions

"Amino acid" refers to naturally occurring amino acids, amino acid analogs, and amino acid mimetics that function in a manner similar to the naturally occurring and analog amino acids. Naturally occurring amino acids are those encoded by the genetic code, as well as those amino acids that are later modified, e.g., hydroxyproline, γ-carboxyglutamate, and O-phosphoserine. Amino acid analogs refers to synthetic amino acids that have the same basic chemical structure as a naturally occurring amino acid, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Both naturally occurring and analog amino acids can be made synthetically. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission.

"Apoptosis" refers to programmed cell death. It is an essential process for normal development and homeostasis in multicellular organisms such as mammals, insects and plants. Apoptosis differs from general cell death as from a toxin or ischemic event in that the cell is shutting down according to a controlled pattern of events. Apoptosis is accompanied by chromosome condensation, by DNA degradation and by its ability to be inhibited by administration of p35.

"Apoptosis-inducing chemical" refers to a chemical that promotes cell programmed cell death. The chemical can be a administered directly to the plant or indirectly by secretion of a pathogen.

"Caspase" refers to a family of cysteine proteases bearing an active site with a conserved amino acid sequence and which cleave specifically following aspartate residues. These proteases were dubbed C(ysteine dependent) ASP (artate cleaving prote)ASE because of the shared structural and functional features. caspase-1 (formerly called ICE, interleukin 1b-converting enzyme, see table 2) was the first member to be identified as a protease involved in mammalian apoptosis because of its homology with CED-3. The latter gene product was known for its requirement in the execution of apoptosis in the nematode C. elegans. To date 10 mammalian members of this family have been identified by structure and substrate specificity. The caspases cleave their substrates after an Asparate in a recognition sequence of 4 amino acids with the conserved Aspartate at position S1 and variability in positions S4-S2 (XXXD). On basis of the recognition sequence the caspase family can be subdivided into three groups. The active site is conserved across the family and has a conserved QACXG (SEQ ID NO:5)(where X is R, Q or G) pentapeptide active site motif. For a general review see Cohen, G. M. 1997. Caspases: the executioners of apoptosis. *Biochem J*. 326:1–16.

"Caspase inhibitors" refers to compounds or peptides which have an inhibitory effect on caspase protease activity. Inhibitor activity is based on concentration-dependent reduction in catalytic activity of a caspase due to substrate-site specific inhibition of the enzyme. For example, inhibition of substrate cleavage by caspase 3 is inhibitor concentration dependent with an $IC_{50}$ of 25 nM for the prototype tetrapeptide inhibitor Ac-DEVD-CHO. The activity of this caspase can be completely blocked by 0.1 uM Ac-DEVD-CHO. Inhibition of caspase activity is dependent on the presence of the aldehyde residue on the alpha carbon at the carboxy terminal amino acid. Minimal inhibition is defined by $IC_{50}$ of 100 nM or less. Selectivity for caspase is meant that the inhibitor is at least twice as potent against a caspase as it is against calpain.

"Exogenous" refers to administration of an inhibitor where the inhibitor is not produced by the plants genes. Soil treatments or foliar sprays are exogenous applications or administrations.

"Heterologous gene" refers to a gene introduced into a host cell via recombinant technology where that gene is either not naturally present in the cell or represents an additional copy of an endogenous gene or is operably linked to a promoter that is not normally found in association with the gene in the host cell.

"Inducible plant promoter" refers to a promoter which directs expression of a gene where the level of expression is alterable by factors such as temperature, pH, transcription factors and chemicals.

"Insecticidal protein" refers to a diverse group of compounds that are lethal to insects when ingested. Examples include the crystal proteins or delta endotoxins from *Bacillus thuringiensis*.

"Non-viral plant disease resistance" refers to the ability of a plant to prevent or inhibit a fungal or bacterial (non-viral) pathogen from successfully infecting plant tissue and causing the symptoms of disease.

"Operably linked" refers to nucleotide sequences which are joined in such a manner that their individual function complements each other. Examples are promoters, transcription terminators, enhancers or activators and heterologous genes which when transcribed and if appropriate to translate will produce a functional product, i.e. a protein, ribozyme or anti-sense construct.

"p35 protease inhibitors" refer to a family of cysteine protease inhibitors derived from the genome of baculoviruses as well as artificially manipulated forms of the inhibitor such as biologically active, fusion proteins, truncated forms and forms with conserved substitutions of the wild-type amino acids.

"Plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

"Plant pathogens" refer to fungi, bacteria and viruses that infect plants and have negative effects on their appearance, growth, production and nutritional quality "Promoter" refers to a region of DNA involved in binding the RNA polymerase to initiate transcription.

"Transformation rate" refers to the percent of cells that are successfully incorporate a heterologous gene into its genome and survive.

"Transfecting" refers to the process of introducing a heterologous gene into a cell.

C. Caspase Inhibitors

Caspase inhibitors are those compositions which have the ability to inhibit caspases, in particular caspase-3 which is also known as CPP32, apopain and Yama. Caspases are a family of related proteases. To date they have not been reported in plants which makes this discovery very unexpected.

In mammals, caspases are members of the interleukin -1β converting enzyme family of cysteine proteases. The enzymes have been generally described in Nicholson et al. *Nature*, 1995, 376:37; Femandes-Alnemri et al. *J. Biol*.

Chem. 1994, 269:30761; and, Tewari et al., *Cell* 1995, 81:801. Substrate targets include poly(ADP-ribose) polymerase (Darmon et al. *Nature,* 1995, 377:446), nuclear lamins (Lazebnik et al. *P.N.A.S. USA,* 1995, 92:9042) and others.

Assays for studying caspases and the effect of inhibitors such as p35 inhibitors are described in the above-recited literature. Conveniently there also is a commercially available kit; BIOMOL QuantiZyme Assay System. This is a Caspase-3 Assay kit designed for Drug Discovery -AK-700 that is available from BIOMOL Research Laboratories, Inc., 5100 Campus Drive; Plymouth Meeting, Pa. 19462.

The BIOMOL caspase assay employs the calorimetric substrate DEVD-p-nitroanilide which upon cleavage has increased absorption at 405 nm. Inhibitors of caspase are assayed by the ability to specifically block DEVD-p-nitroanilide cleavage. For example in a 100 ul reaction containing 30 units of caspase-3 (1 unit is 1 pmol of DEVD-p-nitroanilide cleaved per minute at 25° C.), 0.2 mM DEVD-p-nitroanilide, the activity can be completely blocked by 0.1 uM Ac-DEVD-CHO. Inhibition of caspase 3 is inhibitor concentration dependent with an $IC_{50}$ of 25 nM of the prototype tetrapeptide Ac-DEVD-CHO.

i. Peptide inhibitors.

Caspase inhibitors are well known and are commercially available (Stratagene La Jolla, Calif.). In general they are peptides or peptide analogs that bind to the active site of the caspase enzyme. Among the commercially available tetrapeptides there is: Ac-YVAD-CHO (caspase 1), Ac-WEHD-CHO (caspase 1), Ac-YVKD-CHO (caspase 1 with low specificity), Ac-DEVD-CHO (caspase 3), Ac-DMQD-CHO (caspase 3), Ac-LEVD-CHO (caspase 4), Ac-VEID-CHO (caspase 6), Ac-IETD-CHO (caspase 8), Ac-LEHD-CHO (caspase 9) and Ac-ESMD-CHO. It is possible to synthesize longer peptides or peptides with non-natural linkages such as L peptides, and peptide mimetics with residues that are chemically similar to but are not naturally occurring amino acids such as BAF—boc-aspartyl (OMe)-fluoromethylketone—BAF is a modified amino acid produced by Enzyme Systems Products.

Ac is a acetyl group that blocks the alpha amino group at the amino terminus. However, Ac can be replaced with other functionally equivalent groups such as t-butoxycarbanyl (tBOC). CHO is the aldehyde derivative of the alpha carboxyl group on the carboxy-terminal aspartate acid. CHO can be replaced with other functionally equivalent groups such as fluoromethylketone (FMK) or chloromethylketone (CMK) or dimethylbenzoyloxymethylketone or aldehyde dimethylacetal.

There are commercially available assays for determining the relative potency or selectivity of any novel caspase inhibitor. In general one would expect that a caspase-specific inhibitor to be at least twice as selective as an inhibitor of caspase as for any other cysteine protease such as calpain. Calpain inhibitor (leupeptin) was not effective in blocking apoptotic death or disease in bean or tobacco in experiments we have conducted. Most preferably, the inhibitor should be at least 10× more selective against caspase than other non-caspase enzymes. A conventional means to assay such selectivity by relative potency as measured by $IC_{50}$ where IC is inhibitory concentration.

ii. p35 inhibitors.

There is a known natural source of caspase inhibitors. That source is the insect virus designated baculovirus. Two examples are the p35 inhibitors from *Bombyx mori* nuclear polyhedrosis virus (BmNPV) described in Kamita et al., 1993, *J. Virology,* 67:455–463 and *Autographa californica* NPV (AcNPV) described in Bump et al. *Science,* 1995, 269:1885. The nucleic acid sequence encoding p35 of AcNPV is provided in SEQ ID NO:1. SEQ ID NO:2 provides the amino acid sequence of p35.

In addition to the above functional means to define p35, these proteins can be structurally defined as having at least 70% homology to native forms of protein from wild-type baculovirus. Alternatively they can be defined as being able to bind under stringent conditions to a probe generated from the p35 from AcNPV by PCR using PCR primers:

SEQ ID NO:3: 5'GGCAATAAATTTTAACATTTATT-TAATTGTG 3'

SEQ ID NO:4: 5'TGTGTAATTTTTCCGGTAGAAATC-GAC 3'

Sources of p35.

Protein 35 can be obtained from members of the baculovirus family. Members reported as having p35 include *Bombyx mori* nuclear polyhedrosis virus (BmNPV) described in Kamita et al., supra, and *Autographa californica* NPV (AcNPV) described in Bump et al. supra and the sequence is available from GenBank Accession No. L22858 which provides the entire AcNPV genome and annotates p35.

The p35 nucleic acids of interest can be amplified from viral nucleic acid samples using amplification techniques. For instance, polymerase chain reaction (PCR) technology can be used amplify p35 sequences from any of the baculoviruses identified above.

Appropriate primers and probes for obtaining the p35 sequences from baculovirus are SEQ ID NOS:1 and 2 listed above.

For a general overview of PCR see PCR Protocols: A Guide to Methods and Applications. (Innis, M, Gelfand, D., Sninsky, J. and White, T., eds.), Academic Press, San Diego (1990), incorporated herein by reference.

Polynucleotides encoding p35 may also be synthesized by well-known techniques as described in the technical literature. See, e.g, Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Making Conservative Modifications of caspase inhibitors.

The present invention provides a novel use for caspase inhibitors which includes synthetic peptides and naturally occurring forms, mimetics and analogs. It also includes recombinantly manipulated forms of p35.

Conservatively modified variations of the p35 gene refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are termed silent variations.

Silent variations are particularly important when expressing a heterologous gene where that gene is from a species that does not share the same codon preference as the host cell. Thus it is anticipated that those of skill will want to and can with routine means optimize the p35 gene for best expression in the particular plant host being used to express the p35.

Every nucleic acid sequence herein which encodes a p35 polypeptide also describes every possible silent variation. One of skill will recognize that each codon in a nucleic acid (except AUG, which is ordinarily the only codon for methionine) can be modified to yield a functionally identical molecule by standard techniques.

Accordingly, each silent variation of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are also included so long as the biological properties are essentially unaltered. For example, one of skill could study the two available wild-type proteins and readily ascertain a large number of amino acid changes that could be introduced into either form of p35.

Conservatively modified variations of peptides and p35 also include where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The nucleic acid sequences are preferably optimized for expression in a particular plant host cell used to produce the protein (e.g., a plant cell such as a tomato, or a cloning and expression system such as a yeast cell).

Similarly, conservative amino acid substitutions include those in which one or a few amino acids in an amino acid sequence are substituted with different amino acids with highly similar properties as described above in the listing of related amino acids.

One of skill will recognize many ways of generating alterations in a given nucleic acid sequence of p35, which optionally provides alterations to the encoded protein. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman & Smith, *Gene* 8:81 (1979); Roberts, et al., *Nature* 328:731 (1987) and Sambrook, Innis, Ausubel, Berger, and Mullis (supra) and F. M. Ausubel et al., eds., Current Protocols, a joint venture between Greene Publishing Associates, Inc. and John Wiley & Sons, Inc., (1998 Supplement) (Ausubel).

Most commonly, amino acid sequences are altered by altering the corresponding nucleic acid sequence and expressing the polypeptide. However, polypeptide sequences are also optionally generated synthetically on commercially available peptide synthesizers to produce any desired polypeptide (see, Merrifield, *Science* 232:341–347 (1986), Barany & Merrifield, THE PEPTIDES, Gross & Meienhofer, eds., Academic Press, N.Y., pp. 1–284 (1979); and Stewart & Young, SOLID PHASE PEPTIDE SYNTHESIS, 2d Ed., Pierce Chemical Co., Rockford, Ill., (1984).

Moreover, general knowledge regarding the nature of proteins and nucleic acids allows one of skill to select appropriate sequences with activity similar or equivalent to the nucleic acids, vectors and polypeptides disclosed herein. Exemplar conservative amino acid substitutions are described, supra.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Variants of p35 can also be determined by their ability to bind to SEQ ID NO:1 under stringent conditions. These variants are said to hybridize specifically to their targets, i.e. p35 encoding DNA. The phrases "hybridizing specifically to" or "specific hybridization", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Where a variant is defined by homology to a DNA or amino acid sequence encoding p35. The following terms will assist in defining the limits of the homology defining p35.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Construction of the P35 Expression Vector for Plants i. Basic Methods For Constructing Recombinant Plasmids for Expressing Peptide Inhibitors of Caspase.

Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

Generally, the definitions of nomenclature and descriptions of general laboratory procedures used in this application can be found in the above identified manuals.

All enzymes are used according to the manufacturer's instructions.

Nucleotide sizes are given in either kilobases (kb) or basepairs (bp). These are estimates derived from agarose gel electrophoresis or from published DNA sequences.

Oligonucleotides that are not commercially available can be chemically synthesized according to the solid phase phosphoramidite triester method first described by Beaucage S. L. and Caruthers, M. H. *Tetrahedron Letts.* 22(20) :1859–1862 (1981) using an automated synthesizer, as described in Needham-VanDevanter, D. R., et al., *Nucleic Acids Res.*, 12:6159–6168 (1984). Purification of oligonucleotides is by either native acrylamide gel electrophoresis or by anion-exchange HPLC as described in Pearson, J. D. and Regnier, F. E., *J. Chrom.*, 255:137–149 (1983).

The cloning of p35 requires the use of vectors able to replicate in bacteria. Where Agrobacterium is the means of transformation, shuttle vectors are constructed. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, used to transfect plant cells or incorporated into *Agrobacterium tumefaciens* to infect plants. Cloning in Streptomyces or bacillus is possible.

In order to select the transformed bacteria, selectable markers must be incorporated into the cloning vectors. These markers permit the selection of bacterial colonies containing the vectors which one desires to replicate. Examples of selectable markers include for *E. coli:* genes specifying resistance to antibiotics, i.e., ampicillin, tetracycline, kanamycin, erythromycin, or genes conferring other types of selectable enzymatic activities such as beta-galactosidase, or the lactose operon.

The in vitro delivery of nucleic acids into bacterial hosts can be to any cell grown in culture. Contact between the cells and the genetically engineered nucleic acid constructs, when carried out in vitro, takes place in a biologically compatible medium. The concentration of nucleic acid varies widely depending on the particular application, but is generally between about 1 mM and about 10 mM. Treatment of the cells with the nucleic acid is generally carried out at physiological temperatures (about 37° C.) for periods of time of from about 1 to 48 hours, preferably of from about 2 to 4 hours.

ii. Components of the plant expression cassette

In general, the expressed gene must be driven by a plant promoter (CaMV 35S here) and followed by a transcription terminator (nopaline synthase terminator here). Control of expression is a preferred mode of practice. Control of expression is most easily achieved by selection of a promoter. The transcription terminator is not as critical and a variety of known elements may be used so long as they are recognized by the plant.

There is a wide variety of promoters available to express peptide and p35 protease inhibitors. Those of skill are familiar with the need to optimize each system in accordance with the plant being used to express p35. Expression of the inhibitors can be achieved in all tissues of a regenerated plant using "constitutive" promoters. Constitutive promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the inhibitor gene in a specific tissue or may be otherwise under more precise environmental or developmental control. Such promoters are referred to here as "inducible" promoters. Examples of environmental conditions that may effect transcription by inducible promoters include pathogen attack, anaerobic conditions, ethylene or the presence of light.

Examples of promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations.

Specific types of plant promoters of use in this invention include the dexamethasone inducible promoter described in McNellis, et al., Glucocorticoid-inducible expression of a bacterial avirulence gene in transgenic Arabidopsis induces hypersensitive cell death, *Plant Journal*, 1998 APR, 14(2) :247–257; and a Tet inducible promoter described in GATZ C., et al. Regulation of a Modified CAMV 35S Promoter by the TN10-Encoded TET Repressor in Transgenic Tobacco, *Mol. & Gen. Genetics*, 1991 June, 227(2):229–237.

Other promoters of use in this invention would include the tissue or light regulated promoter described in JofreGarfias, AE; et al., Agrobacterium-medicated transformation of *Amaranthus hypochondriacus:* light- and tissue-specific expression of a pea chlorophyll a/b-binding protein promoter, *Plant Cell Reports, October,* 1997 16(12) :847–852; Liu, ZR et al. Identification of an *Arabidopsis thaliana Ribulose*-1,5-bisphosphate Carboxy-lase Oxygenase Activase (RCA) Minimal Promoter Regulated by Light and the Circadian Clock, *Plant Physiol.*, September, 1996 112(1):43–51; and, Kaiser T., et al., Promoter Elements of the Mustard CHS1 Gene are Sufficient for Light Regulation in Transgenic Plants, *Plant Mol. Biol., May,* 1995 28(2) :219–229.

Because apoptosis is a beneficial process, it is preferred that the p35 be induced under controlled conditions. In general it is preferred that the p35 be either placed under an inducible promoter or in an organ specific promoter such as those identified above.

iii. Shuttle Vectors

Agrobacterium-mediated transformation is a convenient means to transfect p35 genes into a plant. To transform plants using Agrobacterium shuttle vectors are constructed. Shuttle vectors must be able to replicate in each of the hosts and have a selectable marker. There are commercially available vectors for this process and the example section describes such a vector. In brief, the shuttle vectors has one origin of replication for *E. coli* and one for Agrobacterium. They may have selectable markers to differentiate between the bacteria. In the example, the selectable marker is kamomycin for both *E. coli* and Agrobacterium.

Transfecting Plant Cells with Caspase Inhibitors

The DNA constructs of the invention are introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence functions of the *A. tumefaciens* host directs the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.* 3:2717 (1984). Electroporation techniques are described in Fromm, et a., *Proc. Natl. Acad. Sci. USA*, 82:5824 (1985). Ballistic transformation techniques are described in Klein, et al., *Nature*, 327:70–73 (1987).

Alternatively and preferred, the DNA constructs may be combined with suitable T-DNA flanking regions and introduced into a conventional *Agrobacterium tumefaciens* host vector. The virulence functions of the *A. tumefaciens* host will direct the insertion of the inhibitor genes such as the p35 construct and adjacent marker gene(s) (if present) into the plant cell DNA when the cell is infected by the bacteria. For a review of gene transfer methods for plant and cell cultures see, Fisk et al. (1993) *Scientia Horticulturae* 55:5–36 (1993) and Potrykus (1990) CIBA Found. Symp. 154:198.

*Agrobacterium tumefaciens*-meditated transformation techniques are the most commonly used techniques for transferring genes into plants. These techniques are well described in the scientific literature. See, for example Horsch et al. (1984) *Science*, 233:496–498, Fraley et al. (1983) *Proc. Natl. Acad. Sci. USA*, 80:4803, and Hooykaas (1989) *Plant Mol. Biol.*, 13:327–336, Bechtold et al. (1993). *Comptes Rendus De L Academie Des Sciences Serie Iii-Sciences De La Vie-Life Sciences*, 316:1194–1199, Valvekens et al. (1988) *Proc. Natl. Acad. Sci. USA*, 85:5536–5540.

All species which are natural plant hosts for Agrobacterium are transformable in vitro. Most dicotyledonous species can be transformed by Agrobacterium. Monocotyledonous plants, and in particular, cereals, have not previously been regarded as natural hosts to Agrobacterium. There is, however, growing evidence that monocots can be transformed by Agrobacterium. Using recently developed approaches cereal species such as rye (de la Pena et al. (1987) *Nature*, 325:274–276), corn (Rhodes et al. (1988) *Science*, 240:204–207), and rice (Shimamoto et al., (1989) *Nature*, 338:274–276) may now be transformed.

Transformation of a number of woody plants using Agrobacterium and other methods has also been described. (Shuerman et al. (1993) *Scientia Horticulturae*, 55:101–124). For instance, regeneration and transformation of apples is described in James et al. (1989) *Plant Cell Rep.*, 7:658–661.

After transformation, transformed plant cells or plants comprising the introduced DNA must be identified. A selectable and/or scorable marker gene is typically used. Such genes are well known. Transformed plant cells can be selected by growing the cells on growth medium containing the appropriate antibiotic. In some instances, the presence of opines can also be used if the plants are transformed with Agrobacterium.

After selecting the transformed cells, one can confirm expression of the introduced caspase inhibitor gene(s). Simple detection of mRNA encoded by the inserted DNA can be achieved by well known methods in the art, such as Northern blot hybridization. The inserted sequence can be identified using the polymerase chain reaction (PCR) and Southern blot hybridization, as well (see, e.g., Sambrook, et al., *Molecular Cloning—A Laboratory Manual*, Cold Spring Harbor Laboratory, Cold Spring Harbor, N.Y. 1989.).

Regeneration of Transgenic Plants Expressing Inhibitor Peptides and P35

Transformed plant cells, which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., Protoplasts Isolation and Culture, *Handbook of Plant Cell Culture*, pp. 124–176, Macmillian Publishing Company, New York, (1983); and in Binding, Regeneration of Plants, *Plant Protoplasts*, pp. 21–73, CRC Press, Boca Raton, (1985). Regeneration can also be obtained from plant callus, explants, somatic embryos (Dandekar, et al., *J Tissue Cult. Meth.*, 12:145 (1989); McGranahan, et al., *Plant Cell Rep.*, 8:512 (1990)), organs, or parts thereof. Such regeneration techniques are described generally in Klee, et al., *Ann. Rev. of Plant Phys.*, 38:467–486 (1987).

Plants that can be Rendered Disease Resistance

Nucleic acids expressing caspase inhibitors can be used to confer plant disease resistance on essentially any plant. Thus, the invention has use over a broad range of plants, including species from the genera Asparagus, Avena, Brassica, Citrus, Citrullus, Capsicum, Cucumis, Cucurbita, Daucus, Fragaria, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

D. Exigebous Administration of Caspase Inhibitors

Protein agents for agricultural use are formulated like chemical agents. They are usually applied through existing sprayer or spreader technology. The horticultural or agricultural compositions of the invention will include conventional agriculturally accepted agents and additives. Such agents include but are not limited to surface-active agents; such as octylphenol ethoxylate, stabilizers; such as propionic acid, filling agents; such as de-fatted soyflour, flowability or anti-caking agents; such as synthetic precipitated silica, dispersants; such as sodium salt of condensed naphthalene sulfonic acid and the like. The quantity of surface-active agents can vary over a wide range. For convenience such agents may comprise from about 0.1% to about 50% by weight of the composition, more preferably about 0.5% to about 40% and most preferably 1% to about 20%.

The compositions of the present invention may be further formulated, and one skilled in the art is aware of many methods for producing formulated bioagricultural products. These methods are described in the technical and patent literature and include methods for forming granules, wettable powders, water-based and oil-based flowables, concentrates and the like. The following examples are provided for illustration and are not meant to limit the invention in any way.

Wettable powder formulation: 63% active insecticidal ingredients, 10% flow agent (precipitated silica), 4% surfactant (naphthalene sulfonate), 13% dispersant (alkylarylpolyoxy acetate), 7% carrier (attapulgite day), and 3% sequestrant (EDTA).

Granule: 63% active insecticidal ingredients, 20% flow agent (precipitated silica), 3% surfactant (linear alkyl benzene sulfonate), 5% dispersant (blend of anionic surfactant and sodium lignosulfonate), and 9% carrier (kaolin clay).

The inhibitors can be sprayed in an aqueous solution with agriculturally accepted oils, emulsifiers or surfactants to enhance spreadability. Surfactants include detergents such as Triton-X 100 and non-detergent based silane surfactants.

It is expected that the amount and rate of inhibitor will need to be determined on a crop by crop basis. Potency of the inhibitor will also play a role in the determination of application rates. In general, applications rates should produce an application of 1–1000 ug/ml per square meter of leaf surface.

To facilitate the application to large area of plant growth, the inhibitors will be prepared in large scale and sold as a liquid in volumes of a pint or greater, eg. a quart, gallon or 5 gallon containers. Dry solids would be in amounts of a pound or greater.

The compositions of the present invention containing the active ingredients and any further formulations may be used in a method of controlling bacterial, fungi and other plant pathogens on a plant where control is desired comprising applying an effective amount of the composition to the plants.

This invention further anticipates the use of the inhibitors in a spray apparatus where a nozzel emits the inhibitor at a uniform volume under pressure. Such spray apparatus are well known in the industry and are commercially available. The combination of inhibitor and sprayer as a system is considered an invention.

E. Buicgenucak Methods of Assaying for Inhibition of Apoptosis and Plant Resistance by Caspase Inhibitors General methods Apoptosis in plants follows an analogous pathway as in animal cells. Apoptosis can be induced in plants using conventional means such as exposure to cyanide, mannose (1%) or if the plant is susceptible using the various toxins including Fumonisin $B_1$ and AAL-Toxin TA from Alternaria sps. and as described in the examples below.

Two molecular analytic tools are available and established to determine when apoptosis is occurring in plants as distinguished from cell death due to lethal toxins (such as toxic levels of $Fe_2SO_4$) or hypoxic conditions. The first is demonstration of an orderly fragmentation of the cellular DNA. These are called DNA ladders and are readily analyzed using a variety of electrophoretic techniques. The specific gel or running conditions are not critical. Suitable electrophoretic conditions are provided by Wang et al. 1996, Apoptosis: A Functional Paradigm for Programmed Plant Cell Death Induced by a Host-selective Phytotoxin and Invoked During Development, *Cell,* 8:375–391.

Alternatively, fragmentation of DNA during apoptosis can be detected in situ by reagents that react with exposed 3'hydroxyl groups on the nucleosomal units. The assay procedure involves end labeling the DNA fragments by terminal deoxynucleotidyl transferase (TdT) with UTP conjugated to a detectable marker. The method is termed (TUNEL) and more details of this method can be found in Wana et al. (supra). Finally one can visually identify apoptotic bodies containing fragmented DNA which is one of the hallmarks of apoptosis.

Finally, one can determine if apoptosis is a controlling event in the pathogenicity process by administrating an effective amount of a caspase inhibitor in the presence of a pathogen. If the inhibitor imparts or increases disease resistance, one can conclude that the pathogen/host interaction depends upon apoptosis to be successful.

Assaying for plant disease resistance in plants using morphological and other visual indicators.

Once it is established that apoptosis inhibition is due to administration of a caspase inhibitor, those of skill will recognize that it is convenient to assay for disease resistance by traditional methods. These methods involve visual observation of the effects of a pathogen on a host plant. Observable symptoms include wilt, rot, stunted growth, color changes and mycelial growth. The symptoms are scored for their degree of intensity in sufficient repeated trials until statistically meaningful information is generated. The generic experimental parameters for reproducible study of infection and resistance in plants is well known.

Methods for assaying tetrapeptide caspase inhibitors' effect on necrotrophic bacterial diseases of plants A leaf of the susceptible plant of interest is syringe or vacuum infiltrated with a concentration of virulent bacteria sufficient to cause disease and tissue death. A portion of the same leaf or another leaf on the same plant of similar position and age is infiltrated with bacteria and the tetrapeptide inhibitor. Usually a 0.5 mM concentration of inhibitor is sufficient to inhibit disease but may vary according to pathogen and host plant. Disease is permitted to develop under conditions suitable for the plant/pathogen combination. Symptoms are viewed over the course of the experiment to assess the level of symptom (death) inhibition by the caspase inhibitor compared to the control. The affect of the caspase inhibitor on bacterial growth can be assayed by taking samples of the tissue and performing growth curves of the pathogen as described in the literature.

For p35 transformed plants, one simply exposes the plant to the pathogen and compare the disease resistance with appropriate controls such as non-transformed plants.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

EXAMPLE 1

Exogenous Administration of Caspase Inhibitor Peptides and the Method for Screening Efficacy of Peptide Inhibitors of Apoptosis Host plant leaves are infiltrated with bacteria at a suitable concentration ($10^4$–$10^8$ colony forming units per ml) to cause disease. Leaves of the same age and position on the same or a different plant are infiltrated with bacteria of the same concentration with the desired peptide inhibitor added. All solutions are infiltrated directly into the plant leaf lamina with a syringe. Disease symptoms in the form of dead areas of cells are quantified by time lapse color image capture and lesion area measurements determined by digital image analysis. Samples of the control tissue and inhibitor treated tissues are analyzed on a time course basis for bacterial growth rate.

Pathogen growth is measured by grinding leaf disc samples in a suitable buffer followed by serial dilutions and plating of samples onto agar plates to determine the relative number of colonies produced. Colony counts are then related back to the original undiluted samples. Growth values are reported as means of several samples with appropriate statistical measures of mean separation. Differential effects of the inhibitors thus are measured both in terms of the amount of apoptotic cell death induced (symptoms) and by the effect of altering cell death induction on the amount of pathogen growth in the tissue.

Following the above identified procedure, the following bacterial pathogens have been tested and the caspase inhibitors blocked the disease induced by these pathogens.

1) *Pseudomonas syringae* pv. *phaseolicola* in bean leaves
This is a compatible interaction normally resulting in disease and cell death.
Ac-DEVD-CHO blocks cell death
2) *Pseudomonas syringae* pv. *tabaci* in tobacco leaves
This is a compatible interaction normally resulting in disease and cell death.
Ac-DEVD-CHO blocks cell death
Ac-DMQD-CHO blocks cell death
Ac-YVAD-CHO blocks cell death but less well than others
Ac-LRR-CHO (a calpain protease inhibitor) does not block cell death and is used as a control on specificity of the tetrapeptide caspase inhibitors.
3) *Pseudomonas syringae* pv. *angulata* in tobacco leaves
This is a compatible interaction normally resulting in disease and cell death.
Ac-DEVD-CHO blocks cell death
4) *Pseudomonas syringae* pv. *phaseolicola* in tobacco leaves
This is an incompatible interaction normally resulting in no disease but does involve cell death (non-host hypersensitive response).
Ac-DEVD-CHO blocks cell death
Ac-DMQD-CHO blocks cell death
Ac-YVAD-CHO blocks cell death but less well than others
5) *Pseudomonas syringae* pv. *tomato* (avrPto) in tomato (Pto/Pto) leaves
This is an incompatible interaction normally resulting in no disease but does involve cell death (host specific "gene for gene" hypersensitive response)
Ac-DEVD-CHO blocks cell death
Ac-DQMD-CHO blocks cell death
6) *Pseudomonas syringae* pv. *syringae* in tomato leaves.
This is a compatible interaction normally resulting in disease and cell death.
Ac-DEVD-CHO blocks cell death
7) *Pseudomonas syringae* pv. *tomato* in tomato leaves.
This is a compatible interaction normally resulting in disease and cell death.
Ac-DEVD-CHO blocks cell death
Ac-DMQD-CHO blocks cell death
Ac-YVAD-CHO blocks cell death but less well than others
8) *Xanthamonas campestris* pv *tomato* in tomato leaves.
This is a compatible interaction normally resulting in disease and cell death.
Ac-DEVD-CHO blocks cell death.

Hence, these caspase specific inhibitors not only block the diseases associated with each these pathogens but also confirm that the induction of apoptosis is a critical and dependent requirement for disease. This is a basis for the novel discovery that each of these pathogens expresses virulence by inducing apoptosis or programmed cell death and that the blocking of cell death can effectively block disease.

EXAMPLE 2

Construction of a p35 Plant Expression Vector for Tomatoes

Figure 1B:
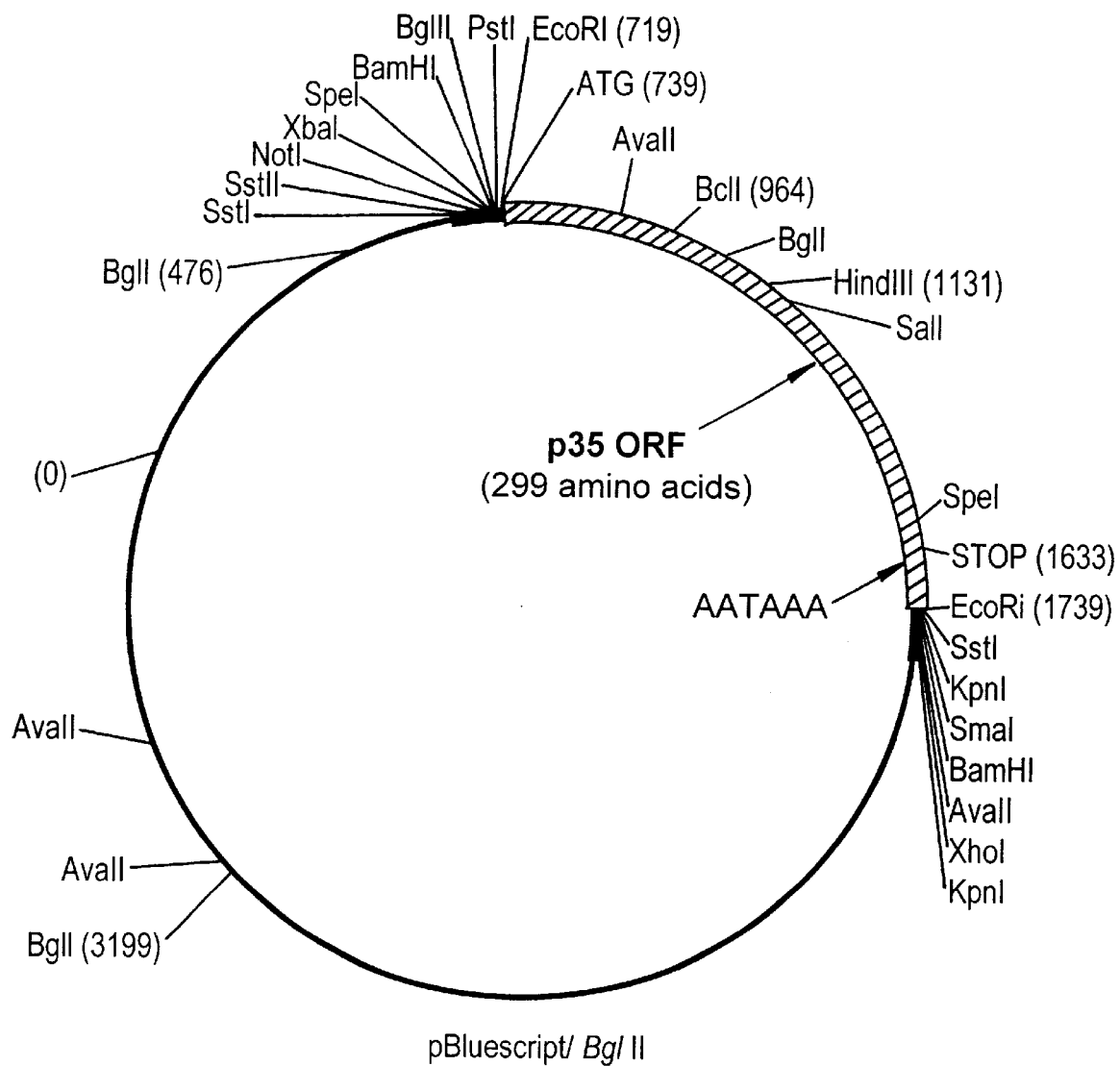

The p35 ORF was obtained from plasmid pPRM-35K-ORF from Paul Friesen (*J. Virol.*, 68:3467–3477 (1994)). The plasmid pPRM-35K-ORF was digested with XbaI and SacI to release the p35 ORF. This fragment was ligated to XbaI and SacI digested pBI121 (available from Clontech located in Palo Alto, Calif.) so as to replace the GUS gene with the p35 gene. This construct was transformed into *E. coli* and selected on kanamycin. The plasmid was then purified and used to transform *Agrobacterium tumefaciens* to kanamycin resistance. The resulting Agrobacterium strain was used to transform tomato cotyledons as described below. The plasmids are described in FIGS. 1(*a*) and (*b*), respectively.

EXAMPLE 3

Transformation of a Tomato Plant with p35

The transformation of tomatoes is in accordance with protocols described in McCormick et al. 1986, *Plant Cell Rpts*, 5:81:84 and Fillate et al. 1987, *Biotechnology*, Jul. 5, 1987. In brief, tomato seeds are surfaced sterilized with bleach and a wetting agent. The seeds are rinsed in distilled water and allowed to germinate on a basic media including Murshige and Skoog salts, sucrose Nitsh's vitamins, inositol and agar at pH 5.8. The seeds are kept moist and dark for 48 hours and germinated in the light at 25 C.

Cotyledon explants are cut from the seedlings in placed upside down on a co-cultivation plate which has tobacco callus tissue.

Agrobacterium in a fresh medium free of antibiotic at concentration of about $5\times10^8$ cells per ml is poured over the explants. The excess bacteria is decanted and the explants are removed and dried and replated. After about 48 hrs. at 25° C., the explants are replated on basic media with Zeatin riboside and allowed to regenerate into shoots. The shoots are cut and placed into rooting media. Rooting is done in the presence of the selection and control antibiotics. The plants are then hardened and tested for genotype and phenotype.

EXAMPLE 4

Genotype Testing

To determine if the plants were expressing p35, DNA was extracted using the CTAB method of DNA isolation described by Ausubel et al. (1995). Short protocols in molecular biology: a compendium of methods from Current protocols in molecular biology/editorial board, Frederick M. Ausubel et al., 3rd ed. [New York]: Wiley, c1995. PCR analysis using primers specific to p35 revealed which segregants were positive for p35 insert.

For Northern analysis, plant RNA was extracted using Trizol (GibcoBRL) and transferred onto a Nytran Plus membrane (Scheicher & Schuell). The dot blot was hybridized with a $^{32}$P-labeled, full-length p35 probe. With rare exceptions, plants having the p35 inhibitor gene demonstrated higher levels of disease resistance than non-p35 transformed plants (see Table 1).

EXAMPLE 5

Assaying for Increased Plant Disease Resistance in the p35 Transformed Tomato

Tomato (*Lycopersicon esculentum*) plants bearing p35 were used for the bioassay were derived from a self-pollinated primary transformant (T1) shown to express p35 transcript. The p35 gene was expressed in plants normally susceptible (asc/asc) to Alternaria stem canker (*Alternaria alternata* f. sp. *lycopercisi*) and Anthracnose (*Colletotrichum coccodes*).

Plants were grown under greenhouse conditions at 22–25° C. and a 16/8 hr. photoperiod until the plants were treated at the 5–6 leaf stage with *A. alternata* f. sp. *lycopersici.* Replications of assays of p35 activity were accomplished on cuttings derived from the mother plants. All fruit harvested for assays were from greenhouse-grown plants.

Cultures of *A. alternata* f sp. *lycopercisi* were grown on potato dextrose agar under fluorescent bulbs on a 12 hr. light/12 hr. dark cycle. Eight to ten day old cultures were imrnersed in water with 0.01% Tween 20 and scraped with a glass rod to dislodge conidia. Conidia were filtered through a double layer of cheesecloth and adjusted to a concentration of $1\times10^5$ conidia/ml. Conidia concentration was ascertained with a hemacytometer.

i. LEAF ASSAYS.

All plants of the segregating population were treated by brushing the spore suspension down the entire length of one side of the stem with a camel hair brush. The lowest, oldest leaf of every plant was also brushed on the adaxial surface with the spore suspension. Several control plants were treated in the same fashion. Control plants included wild-type, non-transgenic susceptible controls (asc/asc), wild-type, non-transgenic resistant controls (Asc/Asc) and GUS-transformed susceptible controls (asc/asc).

All treated plants were placed in a moist chamber (98–100% RH) at 24° C. on a 16/8 hr. photoperiod for 2 days. Plants were removed from the moist chamber and observed for 21 days. Plants were treated in the above manner to ensure that each plant received approximately the same high concentration of inoculum and diminish the possibility of escapes. Any plant recessive at the Asc locus would always die when treated in such a way. Plants were scored for resistance phenotype before knowledge of the genotype of each plant was ascertained.

Spore concentrations of $1\times10^4$, $1\times10^5$ and $1\times10^6$ spores/ml were used to understand the dosage dependent contribution of p35 to resistance. This assay was performed by spraying the entire upper surface of the plants with spore suspension until run-off. Inoculated plants were treated as were the brush-inoculated plants. Spray treatments are likely more typical of a situation occurring in the field.

Segregation analysis revealed a role of p35 in conditioning plant response to the necrotrophic pathogen *Alternaria alternata f.* sp. *lycopersici* (AAL). Resistance to AAL co-segregates with the presence of the transgene in T2 progeny derived from a self of the p35-transforned parent. In plants containing p35 mRNA, a reduction in the rate of symptom development and rate at which the pathogen spreads is evident (Table 1). All susceptible controls (asc/asc) and GUS-transformed susceptible controls died under experimental conditions applied to all individuals. Northern analysis revealed the number of segregants with p35 transcript equals 53 and those without p35 transcript number 11. This ratio suggests that one p35 locus is controlling the interaction between plant and pathogen. The ratio of strongly insensitive to moderately sensitive to susceptible plants scored at 21 days post-inoculation also suggests that one locus is involved (16 strongly insensitive: 32 moderately sensitive: 16 susceptible). The pathogen likely overwhelmed the protective influence of p35 in some hemizygotes which would account for the discrepancy between the number of p35 minus plants (11) and the number of plants dying at 21 days (16).

ii. FRUIT ASSAY

The interaction of p35 and *A. alternataf* sp. *lycopercisi* was further defined by inoculating green fruit. Green fruit was wounded with a hypodermic needle in several locations on the blossom end. Five ml of spore suspension derived as above was placed at the wound site. Spore concentrations of $1\times10^5$ and $5\times10^5$ were used. Treated fruit were placed in a clear plastic box on a wire mesh that held the fruit above a layer of water in the bottom of the box. The plastic box was covered and placed in a growth chamber at 24° C. and 16/8 light/dark cycle for the duration of the experiment. Lesions on fruit developed as circular depressions, the diameters of which were easily measured with a ruler. Mean lesion diameter of lesion on p35-expressing fruit was compared to mean lesion diameter on susceptible control fruit. As with the studies in the tomato leaf sections, the fruits expressing p35 were more resistant to the fungi with p35 expressing fruit showing a 2 to 3 times smaller lesion size than control fruit.

iii. ASSAYS WITH COLLETOTRICHUM COCCODES

Assays with *C. coccodes* were performed on ripe fruit. Fungal cultures were maintained on 30% V8 agar. Eight to ten day old cultures were immersed in water and scraped to dislodge conidia. Conidia suspensions were filtered through 2 layers of cheesecloth and adjusted to $1\times10^5$ spores/ml with a hemacytometer. Ripe fruit was surface sterilized with 70% ethanol and rinsed in sterile water. Wounds in the epidermis of the fruit made with a needle were inoculated with 5 $\mu$l of spore suspension. Inoculated fruit were placed in clear plastic boxes on wire mesh above a layer of warm water. The plastic box was covered and placed in a growth chamber at 24° C. and 16/8 light/dark cycle for the duration of the experiment. Lesions on fruit developed as circular depressions, the diameters of which were easily measured with a ruler. Mean lesion diameter of lesion on p35-expressing fruit was compared to mean lesion diameter on susceptible control fruit. The p35 expressing fruit showed lesions that were one-half the size of control fruit.

The leaf assay for Alternaria toxin was as follows: Young fully expanded leaves of greenhouse grown tomato plants were cut from the plant and incubated for 48 to 72 hours with the cut end immersed in 250 nanomolar TA toxin. Sensitivity to the toxin was visually scored for interveinal regions of death. Comparisons to untransformed tomato showed p35 transformed leaves were much slower to show death.

TABLE 1

Affect of caspase inhibitor p35 on *Alternaria alternata* f. sp. *lycopersici* infection and spread in a population of transgenic tomato plants segregating at the p35 locus.

| Genotype | p35 mRNA* | AAL Disease Severity Index** | Genotype | p35 mRNA* | AAL Disease Severity Index** |
|---|---|---|---|---|---|
| 114-2.1 | y | 2 | 114-2.35 | y | 4 |
| 114-2.2 | y | 4 | 114-2.36 | y | 4 |
| 114-2.3 | y | 5 | 114-2.37 | y | 4 |
| 114-2.4 | n | 5 | 114-2.38 | y | 4 |
| 114-2.5 | y | 5 | 114-2.39 | y | 4 |
| 114-2.6 | y | 5 | 114-2.40 | y | 2 |
| 114-2.7 | y | 5 | 114-2.41 | n | 4 |
| 114-2.8 | y | 2 | 114-2.42 | y | 1 |
| 114-2.9 | y | 2 | 114-2.43 | y | 4 |
| 114-2.10 | y | 3 | 114-2.44 | y | 5 |
| 114-2.11 | n | 5 | 114-2.45 | y | 5 |
| 114-2.12 | y | 3 | 114-2.46 | y | 4 |
| 114-2.13 | y | 1 | 114-2.47 | y | 4 |
| 114-2.14 | y | 5 | 114-2.48 | n | 5 |
| 114-2.15 | y | 2 | 114-2.49 | y | 5 |
| 114-2.16 | y | 5 | 114-2.50 | y | 5 |
| 114-2.17 | y | 2 | 114-2.51 | y | 4 |
| 114-2.18 | y | 4 | 114-2.52 | y | 5 |
| 114-2.19 | y | 3 | 114-2.53 | y | 5 |
| 114-2.20 | y | 5 | 114-2.54 | n | 5 |
| 114-2.21 | n | 4 | 114-2.55 | y | 1 |
| 114-2.22 | n | 4 | 114-2.56 | y | 1 |
| 114-2.23 | y | 2 | 114-2.57 | y | 5 |
| 114-2.24 | y | 4 | 114-2.58 | y | 4 |
| 114-2.25 | n | 4 | 114-2.59 | y | 3 |
| 114-2.26 | n | 5 | 114-2.60 | n | 5 |
| 114-2.27 | y | 2 | 114-2.61 | y | 5 |
| 114-2.28 | y | 2 | 114-2.62 | y | 3 |
| 114-2.29 | n | 5 | 114-2.63 | y | 5 |
| 114-2.30 | y | 4 | 114-2.64 | y | 5 |
| 114-2.31 | y | 3 | | | |
| 114-2.32 | y | 4 | asc/asc | n | 5 |
| 114-2.33 | y | 1 | 35S::GUS | n | 5 |
| 114-2.34 | y | 4 | ASC/ASC | n | 0 |

*Determined by Northern blot with full-length p35 insert as probe.
**Disease severity assessed by comparing treated plants with susceptible and resistant control plants 21 days post-inoculation: 0 = no disease symptoms; 1 = petiole lesions evident, <half stem with lesions; 2 = petiole lesions evident, all of stem with lesions; 3 = petiole and stem lesions expanding; 4 = petiole and stem lesions expanding, toxin symptoms on leaves; 5 = plant dead.

```
Sequence ID No.1.
P35 sequence=
ATGTGTGTA ATTTTTCCGG TAGAAATCGA CGTGTCCCAG ACGATTATTC

GAGATTGTCA GGTGGACAAA CAAACCAGAG AGTTGGTGTA CATTAACAAG

ATTATGAACA CGCAATTGAC AAAACCCGTT CTCATGATGT TTAACATTTC

GGGTCCTATA CGAAGCGTTA CGCGCAAGAA CAACAATTTG CGCGACAGAA

TAAAATCAAA AGTCGATGAA CAATTTGATC AACTAGAACG CGATTACAGC

GATCAAATGG ATGGATTCCA CGATAGCATC AAGTATTTTA AAGATGAACA

CTATTCGGTA AGTTGCCAAA ATGGCAGCGT GTTGAAAAGC AAGTTTGCTA

AAATTTTAAA GAGTCATGAT TATACCGATA AAAAGTCTAT TGAAGCTTAC

GAGAAATACT GTTTGCCCAA ATTGGTCGAC GAACGCAACG ACTACTACGT

GGCGGTATGC GTGTTGAAGC CGGGATTTGA GAACGGCAGC AACCAAGTGC

TATCTTTCGA GTACAACCCG ATTGGTAACA AAGTTATTGT GCCGTTTGCT

CACGAAATTA ACGACACGGG ACTTTACGAG TACGACGTCG TAGCTTACGT
```

-continued

```
GGACAGTGTG CAGTTTGATG GCGAACAATT TGAAGAGTTT GTGCAGAGTT

TAATATTGCC GTCGTCGTTC AAAAATTCGG AAAAGGTTTT ATATTACAAC

GAAGCGTCGA AAAACAAAAG CATGATCTAC AAGGCTTTAG AGTTTACTAC

AGAATCGAGC TGGGGCAAAT CCGAAAAGTA TAATTGGAAA ATTTTTTGTA

ACGGTTTTAT TTATGATAAA AAATCAAAAG TGTTGTATGT TAAATTGCAC

AATGTAACTA GTGCACTCAA CAAAAATGTA ATATTAAACA CAATTAAATA

A
```

Seq. ID. No.2
P35 translation=
MCVIFPVEIDVSQTIIRDCQVDKQTRELVYINKIMNTQLTKPVL

MMFNISGPIRSVTRKNNNLRDRIKSKVDEQFDQLERDYSDQMDGFHDSIKYFKDEHYSVS

CQNGSVLKSKFAKILKSHDYTDKKSIEAYEKYCLPKLVDERNDYYVAVCVLKPGFENGS

NQVLSFEYNPIGNKVIVPFAHEINDTGLYEYDVVAYVDSVQFDGEQFEEFVQSLILPSSFK

NSEKVLYYNEASKNKSMIYKALEFTTESSWGKSEKYNWKIFCNGFIYDKKSKVLYVKLH

NVTSALNKNVILNTIK

PCR Primers for p35=
Seq. ID No. 3: 5'GGCAATAAATTTTAACATTTATTTAATTGTG 3'

Seq. ID No. 4: 5'TGTGTAATTTTTCCGGTAGAAATCGAC 3'

---

What is claimed is:

1. A method of increasing non-viral plant disease resistance in a plant said method comprising expressing a gene encoding a p35 protease inhibitor of baculovirus in the plant in an amount sufficient to increase non-viral plant disease resistance in the plant wherein the disease is caused by a pathogen/plant interaction that depends on apoptosis to be successful.

2. A method of claim 1, where the p35 protease inhibitor gene is operably linked to an inducible plant promoter.

3. A method of claim 1, wherein the gene is a stably incorporated gene encoding p35 protease inhibitor wherein the gene has codons selected to be those preferably used by the host plant.

4. A method of inhibiting chemically-induced apoptosis in a plant or plant cell comprising transforming the cell with a gene encoding p35 protease inhibitor of baculovirus and exposing the plant or plant cell to apoptosis-inducing chemicals.

5. A method of claim 4, wherein the apoptosis-inducing chemicals are from plant pathogens.

6. A method of claim 5, wherein the pathogens are fungal.

7. A plant having increased plant disease resistance against non-viral pathogens wherein the increased plant disease resistance is due to the stable expression of a p35 protease inhibitor of baculovirus in the plant in an amount sufficient to increase non-viral plant disease resistance in the plant wherein the disease is caused by a pathogen/plant interaction that depends on apoptosis to be successful.

8. A plant of claim 7, wherein the plant is selected from the group consisting of graminaceae, solanaceae, rosaceae, compositeae, leguminaceae, brassicaceae, and cucurbitaceae.

* * * * *